(12) United States Patent
Neuberger et al.

(10) Patent No.: US 9,724,069 B2
(45) Date of Patent: Aug. 8, 2017

(54) TISSUE RESECTION UNDER IMAGE GUIDANCE/CONTROL

(75) Inventors: Wolfgang Neuberger, Dubai (AE); Manfred Kistner, Düsseldorf (DE)

(73) Assignee: biolitec Unternehmensbeteiligungs II AG, Vienna (AT)

(*) Notice: Subject to any disclaimer, the term of this patent is extended or adjusted under 35 U.S.C. 154(b) by 197 days.

(21) Appl. No.: 12/976,337

(22) Filed: Dec. 22, 2010

(65) Prior Publication Data
US 2011/0319757 A1    Dec. 29, 2011

Related U.S. Application Data

(60) Provisional application No. 61/288,980, filed on Dec. 22, 2009.

(51) Int. Cl.
| | |
|---|---|
| *A61B 5/05* | (2006.01) |
| *A61B 8/08* | (2006.01) |
| *A61N 5/06* | (2006.01) |
| *A61B 8/12* | (2006.01) |
| *A61B 18/24* | (2006.01) |
| *A61B 18/00* | (2006.01) |
| *A61B 18/18* | (2006.01) |
| *A61B 90/00* | (2016.01) |

(52) U.S. Cl.
CPC ............. *A61B 8/0841* (2013.01); *A61B 8/12* (2013.01); *A61B 18/24* (2013.01); *A61N 5/0601* (2013.01);
(Continued)

(58) Field of Classification Search
CPC .......... A61B 18/24; A61B 2018/00547; A61B 2018/1807; A61B 2090/3762; A61B 2090/3764
(Continued)

(56) References Cited

U.S. PATENT DOCUMENTS

| | | | | |
|---|---|---|---|---|
| 5,370,121 A | * | 12/1994 | Reichenberger et al. | 600/438 |
| 5,391,197 A | * | 2/1995 | Burdette et al. | 601/3 |

(Continued)

OTHER PUBLICATIONS

Biolitec, EVOLVE Fibers, http://www.biolitec-us.com/twister.html, 2007.*
(Continued)

*Primary Examiner* — Joel Lamprecht
(74) *Attorney, Agent, or Firm* — BJ Associates; Bolesh J. Skutnik

(57) ABSTRACT

An improved method and device for accurate, efficient surgical procedures are disclosed. The disclosed system consists in simultaneously using an elongated member that conveys energy to a treatment site and imaging means to control position of the elongated member and monitor treatment progress in real-time. In a preferred embodiment, for BPH, a twister fiber with a fused cap is used and ultrasound image guidance is obtained using a rectal probe. The method consists in placing an ultrasound rectal probe, fixed by mechanical means, and an optical fiber inserted into urethra. Initial positioning of probe is done under endoscopic/ultrasound control. The twister fiber probe operates in contact-mode. Treatment is monitored, real-time, by the ultrasound device. Additional imaging technologies include Positron Emission Tomography (PET), Computed Tomography (CT) or Optical Coherence Tomography. Other applications include the removal of tumorous (hyperplasic) tissue. Sources include lasers, higher power LEDs or bright lamps and photodynamic therapy.

18 Claims, 2 Drawing Sheets

(52) U.S. Cl.
CPC ............... *A61B 2018/00547* (2013.01); *A61B 2018/1807* (2013.01); *A61B 2090/3762* (2016.02); *A61B 2090/3764* (2016.02); *A61B 2090/3784* (2016.02)

(58) Field of Classification Search
USPC ....... 600/101, 104–108, 437, 439, 459, 462; 128/898
See application file for complete search history.

(56) References Cited

U.S. PATENT DOCUMENTS

| | | | |
|---|---|---|---|
| 5,495,541 A * | 2/1996 | Murray et al. | 385/33 |
| 6,699,239 B1 * | 3/2004 | Stiller et al. | 606/15 |
| 6,824,516 B2 * | 11/2004 | Batten et al. | 600/439 |
| 2001/0049350 A1 * | 12/2001 | Cincotta | A61K 31/166 514/11.5 |
| 2002/0040185 A1 * | 4/2002 | Atalar et al. | 600/423 |
| 2007/0230757 A1 * | 10/2007 | Trachtenberg et al. | 382/128 |
| 2009/0198094 A1 * | 8/2009 | Fenster et al. | 600/3 |

OTHER PUBLICATIONS

Farsi et al, Visual Laser Ablation of the Prostate (VLAP) With Bare Fiber in Conjunction With Laser Bladder Neck Incision in the Treatment of Patients With Benign Prostatic Hyperplasia (BPH), Annals of Saudi Medicine, vol. 17, No. 2, 1997, pp. 191-194.*

* cited by examiner

TISSUE RESECTION UNDER IMAGE GUIDANCE/CONTROL

DOMESTIC PRIORITY UNDER 35 USC 119(e)

This application claims the benefit of U.S. Provisional Application Ser. No. 61/288,980 by Wolfgang Neuberger and Manfred Kistner, entitled "TISSUE RESECTION UNDER IMAGE GUIDANCE/CONTROL" filed Dec. 22, 2009, which is incorporated by reference herein.

BACKGROUND OF THE INVENTION

1. Field of the Invention

The present invention relates to laser systems for medical treatments and in particular, for laser surgical procedures. More particularly, it relates to optical fiber systems and methods used for the treatment of various image guided surgical procedures, such as benign prostatic hyperplasia under echographic imaging.

2. Information Disclosure Statement

Many important medical conditions suffered by many patients require treatments which consist of removing abnormal soft tissue from the body. Undesired tissue may include tumors and atheromatous plaques, excess fat in aesthetic treatments, or portions of prostate tissue. In urology, for example prostate disorders such as cancer or benign enlarged prostate (BPH) require this tissue to be partially or totally removed.

Tissue removal can be performed by means of different methods. Independently of the method used, the main objective of this kind of treatment is the removal of the whole undesired tissue while preventing from damage of surrounding tissue. In recent years, laser energy has been used in order to accomplish this aim.

Based on laser energy application on tissue, numerous approaches have been proposed. Laser techniques are usually preferred due to its special capacity of delivering high amounts of power on reduced areas, thus improving treatment precision and efficiency and diminishing undesired effects on surrounding tissue.

Prostate cancer affects over 232,000 men in the US every year. It is a malignant tumor growth that consists of cells from the prostate gland. The tumor usually grows slowly and remains confined to the gland for many years. During this time, the tumor produces little or no symptoms or outward signs (abnormalities on physical examination). As the cancer advances, however, it can spread beyond the prostate into the surrounding tissues. Moreover, the cancer also can metastasize throughout other areas of the body, such as the bones, lungs, and liver.

Benign prostatic hyperplasia (BPH) or "enlarged prostate" refers to the noncancerous (benign) growth of the prostate gland. While BPH is the most common prostate problem in men over 50 years of age, benign growth of the prostate begins with microscopic nodules around 25 years of age, although it rarely produces symptoms before a man reaches 40. It is estimated that 6.3 million men in the United States have BPH and the disease is responsible for 6.4 million doctor visits and more than 400,000 hospitalizations per year.

The exact cause of BPH is unknown but it is generally thought to involve hormonal changes associated with the aging process. Testosterone likely has a role in BPH as it is continually produced throughout a man's lifetime and is a precursor to dihydrotestosterone (DHT) which induces rapid growth of the prostate gland during puberty and early adulthood. When fully developed, the prostate gland is approximately the size of a walnut and remains at this size until a man reaches his mid-forties. At this point the prostate begins a second period of growth which for many men often leads to BPH later in life.

In contrast with the overall enlargement of the gland during early adulthood, benign prostate growth occurs only in the central area of the gland called the transition zone, which wraps around the urethra. As this area of the prostate grows, the gland presses against the urethra, leading to difficult or painful urination. Eventually, the bladder itself weakens and loses the ability to empty by itself.

Obstructive symptoms such as intermittent flow or hesitancy before urinating can severely reduce the volume of urine being eliminated from the body. If left untreated, acute urine retention can lead to other serious complications such as bladder stones, urinary tract infections, incontinence, and, in rare cases, bladder and kidney damage. These complications are prevalent in older men who are also taking anti-arrhythmic drugs or anti-hypertensive (non-diuretic) medications. In addition to the physical problems associated with BPH, many men also experience anxiety and a reduced quality of life.

Mild symptoms of BPH are most often treated with medication such as alpha-blockers and anti-androgens.

Men suffering with moderate to severe BPH symptoms must typically undergo surgery. There are a number of surgical methods for treatment of BPH. Transurethral resection of the prostate (TURP) has been widely used, but causes a number of complications including bleeding, incontinence, retrograde ejaculation and impotence. An alternative surgical method is transurethral incision of the prostate (TUIP). Incisions are made in the prostate to relieve pressure and improve flow rate. Incisions are made where the prostate meets the bladder. No tissue is removed in the TUIP procedure. Cutting muscle in this area relaxes the opening to the bladder, which decreases resistance to urine flow from the bladder. A variant of the TUIP procedure in which a laser is used to make the incision is the transurethral laser incision of the prostate (TULIP). This method is effective but it's known to cause numerous side effects, including incontinence, impotence, retrograde ejaculation, prolonged bleeding and TURP syndrome.

Photodynamic therapy has also been proposed for treatment of prostatic conditions. For example, Rubinchik et al. disclose in U.S. Patent Publication 2008/0071331A1 a method for treating BPH, comprising the administration of a photosensitizer by direct injection into the prostate tissue of a subject afflicted with or suspected of being afflicted with a prostatic disorder; and irradiation of the prostate tissue with energy at a wavelength appropriate to activate the photosensitizer. Imaging means such as MRI, X-ray, or ultrasound may be used to assess correct placement of injection device. In addition to conventional PDT disadvantages, in this method treatment progress is not assessed by imaging means. As a consequence, treatment precision may be inadequate, thus leading to uncertain results or affecting healthy tissue.

Other surgical techniques used for BPH treatment include methods for causing necrosis of the tissue that blocks the urethra. Hyperthermic methods, for example, use the application of heat to kill unwanted cells, which will gradually be absorbed by the body. Several methods of applying heat or causing necrosis have been used, including direct heat (transurethral needle ablation, or TUNA), ultrasound (high-intensity focused ultrasound, or HIFU), and electrical vaporization (transurethral electrical vaporization of the prostate, or TUEVP). However, the amount of intervention time required to eliminate large amounts of tissue can result in strain and stress on the patient who is usually fully conscious during the intervention. The extensive period of time required is also a cost factor for the operating urologist.

For cancer, when it is detected before metastasis, laser surgery employing side-firing fibers is a preferred treatment among surgeons and patients. It causes little blood loss and allows for a shorter recovery time.

At present, the preferred treatment by those skilled in the art is laser ablation of undesired tissue. There are a number of different laser techniques in which light is used to eliminate excess of prostate tissue either by ablation (vaporization), thermal coagulation or a combination of both these mechanisms. The observed clinical effects are due to the absorption of light (by the target tissue itself and/or surrounding fluids) and subsequent heat transfer, the extent of which largely depends on the power and wavelength of the impinging laser beam.

Most types of laser surgeries are able to provide an immediate improvement in the urinary stream. Laser surgery for BPH has other potential advantages over prior art techniques, such as reduced blood loss as well as shorter treatment times, faster patient recovery, and lower risk of post-treatment incontinence. However, many patients still require catheterization for 1-2 weeks post-treatment after undergoing some forms of laser surgery.

An important factor determining the success of laser surgery in urology is the accuracy with which the surgeon is able to eliminate undesired prostate tissue in order to achieve adequate tissue ablation without damaging surrounding healthy tissue. To accomplish this accuracy, it is necessary to meet at least two requirements: using an appropriate optical fiber and an effective imaging means. Needless to say, laser source should have adequate emission features for performing required treatments.

Regarding optical fibers, inventors have worked over the years on developing diverse optical fiber configurations that can improve efficiency, accuracy and thus safety of the procedure. Fibers must also be able to withstand the high laser energy emitted by new laser source technologies. In BPH treatment, laser beams oriented at a certain angle with respect to the fiber's main axis are preferred. This way, surgeons can limit their lasing to back and forth and rotational movements while they observe the procedure by endoscopy. Several patents disclose different variants of side-firing configurations. Some examples are U.S. Pat. No. 5,292,320 by Brown et al., U.S. Pat. No. 5,509,917 by Cecchetti et al., U.S. Pat. No. 5,366,456 by Rink et al., U.S. Patent Publication 2006/0285798 by Brekke et al., and U.S. Pat. No. 5,416,878 by Bruce.

Recently, Neuberger described in application Ser. No. 12/714,155 a twister fiber, which represents a substantial improvement over prior art, allowing for safer, more accurate and less time consuming procedures. The disclosed device comprises a bent tip fiber with a fused cap as an integral part of it placed at its distal (output) end and with a rotatable connector at the proximal (input) side. Fiber tip may be constructed with different shape configurations, such as a convex tip to improve focusing characteristics, a concave tip to achieve diverging irradiation, or an expanded beam tip to achieve an effect similar to that obtained by electrosurgical tools. A grip guarantees and enhances the ability to twist and rotate it easily. Optical fiber's steerability, twistability and rotation lead to a more precise an improved effect on tissues. Thus, easier, faster and more precise and efficient treatments can be performed. Twister fibers emit light in several directions and carbonization occurs on its surface; most likely in some preferred areas. Since twister fiber is operated in contact-mode, carbonized areas at surface create hot spots that can be used to remove tissue. As a consequence, improved and enhanced treatment of diverse pathologies can be performed, making it possible to efficiently and easily reach and treat specific tissues.

Twister fiber might be inserted, for instance, into an endoscope to perform high power vaporization of prostatic tissue for BPH treatments. Furthermore, it might be steered into one of the prostatic lobes, which might be excavated from the inside in order to relieve pressure on the urethra while maintaining the urethra's integrity as much as possible. Other applications of twister fiber include removal of tumorous (hyperplasic) tissue or other unwanted tissue from the body.

As previously mentioned, in addition to an adequate optical fiber, it is also vital to use an appropriate and effective imaging means in order to achieve a successful treatment. During BPH treatment, field of view may be limited, as the fiber tip is outside cystoscope while endoscopic camera is inside cystoscope. Furthermore, hot spots will cause fiber to enter tissue and therefore, fiber tip will get out of field of view. Other situations may "blind" endoscope lens, such as excessive bleeding, vaporization bubbles and anatomical structures at difficult angles of vision. Thus, endoscopic view may at times result insufficient to continuously monitor the procedure and make sure only unwanted tissue is being ablated. As a consequence, a complementary reliable and noninvasive device and method that can help evaluate tissue damage during laser procedures in real time is needed.

Imaging/control means have been historically used for assessing the amount of tissue damage and for positioning optical fiber. In order to improve tissue damage evaluation and fiber positioning, different approaches have been developed for complementing endoscopy. Some computer modeling techniques intend to predict tissue thermal damage according to different heat transfer theories and knowledge of tissue properties. These methods, without some imaging backup, are still unreliable due to tissue heterogeneity existing in the treated area regarding physical properties, geometry and blood perfusion.

Methods such as thermocouple or light-detector insertion can also provide information about the light distribution or heat development at different points in the tissue. These parameters may be used as feedback tools for laser adjustment during therapy to achieve optimal localized tumor destruction. However, effectiveness is limited because probe insertion is invasive. Furthermore, sites that can be sensed are limited.

Several imaging methods have been proposed to accompany direct endoscopic viewing in order to follow tissue response during laser therapy in medical treatments that require precision to assure treatment efficacy and patient safety. Imaging modalities presently available for the acquisition of clinical images during medical procedures include 2D X-ray imaging, computed tomography, magnetic resonance imaging, 2D radioisotope imaging, single photon emission computed tomography, positron emission tomography, thermography, and transillumination. For example, U.S. Pat. No. 6,684,097 by Parel et al discloses a device for monitoring thermally-induced changes to localized regions of tissue. The device has an X-ray illumination source, an X-ray detector, a data storage unit in communication with the X-ray detector, an image comparison unit and an image display unit in communication with the image comparison unit. The tissue to be monitored is a portion of a patient's body which is being monitored during the surgical procedure. The resultant image signal is a difference image signal that is generated by the image comparison unit and then displayed on an image display unit to provide real-time information concerning the temperature distribution and changes in temperature throughout the portion of the patient's body being monitored. This technology is complex and difficult to apply and requires expensive equipment. Moreover, some of these techniques require considerable processing time before achieving a useful image, thus impeding a real time control of the procedure.

In urologic procedures such as BPH treatment or prostate cancer treatment, ultrasonography has been preferred by those skilled in the art as a practical low-cost and reliable means of identifying essential landmarks and of controlling applied energy action. In medical ultrasound imaging, pulses of longitudinal sound waves at frequencies from 1 to 20 MHz are emitted by one or more piezoelectric transducers into the body volume being imaged. Inside the body, ultrasound is attenuated through scattering and absorption. The intensities and arrival times of ultrasound waves reflected back to the transducer by internal acoustic boundaries are measured and converted into images of the reflecting boundaries. For sound waves, a boundary is a spatial discontinuity in the acoustic impedance, defined in any medium as the product of the speed of sound and density. Speed of sound, and acoustic impedance are temperature dependant.

Some approaches have been proposed for enhancing ultrasound detection of surgical devices inserted into the body. For example, Fry in U.S. Pat. No. 4,582,061 discloses a needle with ultrasonically reflective displacement scale, a puncturing device for insertion into the body, which has an ultrasonically coded displacement scale of gaseous inclusions regularly spaced along the length of the device. Owing to the acoustic reflectiveness of the gaseous inclusions, the precise location of the puncturing device can be directly and readily detected by an ultrasound visualization system. The acoustically reflective displacement scale enables the calibration of distances to be made directly from the ultrasound viewing screen. Located at the tip of the puncturing device is a gaseous inclusion which reveals the precise location of the tip of the device in the body.

In order to ultrasonically assess surgical treatments, some inventors have come up with different ideas. For instance, in U.S. Pat. No. 5,657,760, Ying et al. disclose an apparatus for ultrasonic Doppler monitoring of the extent and geometry of tissue damage resulting from thermal therapy. An embodiment of this invention comprises a laser fiber optic incorporated into an ultrasound transducer with the sound and laser beams collinear. As Doppler probe is collinear with fiber, in urologic laser treatments such as BPH, both probe and laser fiber (and endoscopic fiber) are inserted into the urethra. Cystoscopes usually also include a canal for flushing liquid into the urethral canal. Insertion of a device with several canals and apparatus into the urethra canal can cause a series of complications and may also make procedure more complex, requiring extreme care by physician. Furthermore, a special cystoscope for supporting numerous channels is needed, with a larger diameter than regular cystoscopes, thus causing an increased patient discomfort.

Those skilled in the art prefer images obtained by a probe inserted in a different angle such as those generated to diagnose prostate conditions. For example, transrectal ultrasound (TRUS) tests estimate the size of prostate gland and can be helpful in diagnosing or ruling out prostate cancer. After a lubricating gel is applied to rectum, the ultrasound probe, about the size and shape of a large cigar, is inserted for imaging the prostate and surrounding tissue. These ultrasound imaging procedures give important information on condition of the prostate and its anatomic surrounding, which is useful previous to the intervention. Furthermore, ultrasound imaging can give a physician valuable information during treatment especially when excessive bleeding, vaporization bubbles or anatomical structures at difficult angles of vision are present.

There is therefore a need for a laser treatment system that improves on the state of the art by allowing more precise and clear online view of treated area when maneuvering high power side firing laser beam transmission for eliminating abnormal soft tissue such as cancerous or hyperplasic prostate tissue. The present invention addresses this need.

OBJECTIVES AND BRIEF SUMMARY OF THE INVENTION

It is an objective of the present invention to provide a device and method for improved surgical procedures, such as urological treatments and tissue ablation.

It is also an objective of the present invention to provide a device and method for faster, safer, more precise, and more reliable treatment to achieve effective laser irradiation of unwanted tissue while preserving surrounding healthy tissue.

It is another objective of the present invention to provide a device and method for improved laser surgical procedures, enhanced by real-time image guidance of the resecting/denaturating device.

It is still another objective of the present invention to provide a surgical device and method for the removal of tumorous or hyperplasic tissue or other unwanted tissue in the body.

It is yet another objective of the present invention to treat benign prostatic hyperplasia by means of vaporization of prostatic tissue as well as lobe excavation under ultrasound guidance.

Briefly stated, an improved method and device for safe, accurate and efficient surgical procedures are disclosed. The disclosed system consists in the simultaneous use of an elongated member that conveys energy to a site to be treated and an imaging means to control position of the elongated member and to monitor progress of treatment in real-time. Preferably, elongated member is a laser probe and imaging means is an ultrasound device, but not limited thereto. In a preferred embodiment, for BPH procedures, a bent tip fiber with a fused cap, i.e. twister fiber, is used and ultrasound image guidance is obtained by means of a rectal probe. Since twister fiber is operated in contact-mode, carbonized areas at surface create hot spots that can be used to remove tissue. As a consequence, improved and enhanced treatment of diverse pathologies can be performed, making it possible to efficiently and easily reach and treat specific tissues. The method described consists in placing an ultrasound rectal probe and fixing it by some mechanical means, with patient in lithotomy position. Then, optical fiber is inserted into urethra. This may be done directly or through a cystoscope. Initial positioning of laser probe is done under endoscopic (if present) and/or ultrasound control and laser treatment begins, operating the twister fiber probe in contact-mode. Treatment progress is monitored in real-time by the ultrasound device. Additional imaging technologies may be used including but not limited to Positron Emission Tomography (PET), Computed Tomography (CT) or Optical Coherence Tomography. In addition to BPH treatment, other applications include the removal of tumorous (hyperplasic) tissue or other unwanted tissue in other areas within the body. Laser sources of various wavelengths can be used, but also higher power LED devices or bright lamps and photodynamic therapy. Device and method described present numerous advantages: physician is able to see real time progress of treatment guided by ultrasound view, injuries of capsule and accidental ablation of healthy tissue can be avoided as clear ultrasound view is provided at any time of the treatment procedure and the treatment is faster and safer. Furthermore, patient comfort is enhanced due to the possibility of inserting treatment elongated member without an endoscope, rendering a less invasive treatment.

The above and other objects, features and advantages of the present invention will become apparent from the following description read in conjunction with the accompanying drawings.

DETAILED DESCRIPTION OF PREFERRED EMBODIMENTS

As previously mentioned, the accuracy with which the surgeon is able to eliminate undesired tissue greatly determines laser surgery success. At least two requirements must be met in order to perform a successful procedure: using an appropriate optical fiber and effective imaging means.

Regarding optical fibers, several approaches have been developed for improving efficiency, accuracy and thus safety of the procedure. Recently developed, the twister fiber (an optical fiber comprising an off-axis firing end) represents a substantial improvement over prior art, allowing for safer, more accurate and less time consuming procedures. With respect to effective imaging and controlling means, some approaches have also been proposed. During BPH treatment, field of view may be limited, as the fiber tip is outside cystoscope while endoscopic camera is inside cystoscope. Furthermore, hot spots will cause fiber to enter tissue and therefore, fiber tip will get out of field of view. Thus, endoscopic view may at times be insufficient to continuously monitor the procedure and make sure only unwanted tissue is being ablated. Those skilled in the art prefer images obtained by a probe inserted in a different angle with respect to laser fiber. As a consequence, transrectal ultrasound (TRUS) may be used complementing endoscopy to estimate the size of prostate gland and can be helpful in diagnosing or ruling out prostate cancer.

In addition, current preferred treatment is laser ablation. In this technique, laser source should have adequate emission features for performing different treatments.

In this invention, a system is disclosed consisting in the simultaneous use of an elongated member that conveys energy to a site to be treated and an imaging means to control position of the elongated member and to monitor progress of treatment in real-time. Preferably, elongated member is a laser probe and imaging means is an ultrasound device, but not limited thereto. Using this system, physician is able to see real time progress of treatment guided by ultrasound view, injuries of capsule can be avoided as clear ultrasound view is provided at any time of the treatment procedure and the treatment is faster and safer. Furthermore, patient comfort is enhanced due to the possibility of inserting treatment elongated member without an endoscope. As a consequence, treatment renders less invasive due to the reduced diameter of inserted items into urethra. This is based on the well-defined and valuable information that current state of the art ultrasound technology can provide.

Figure 1:
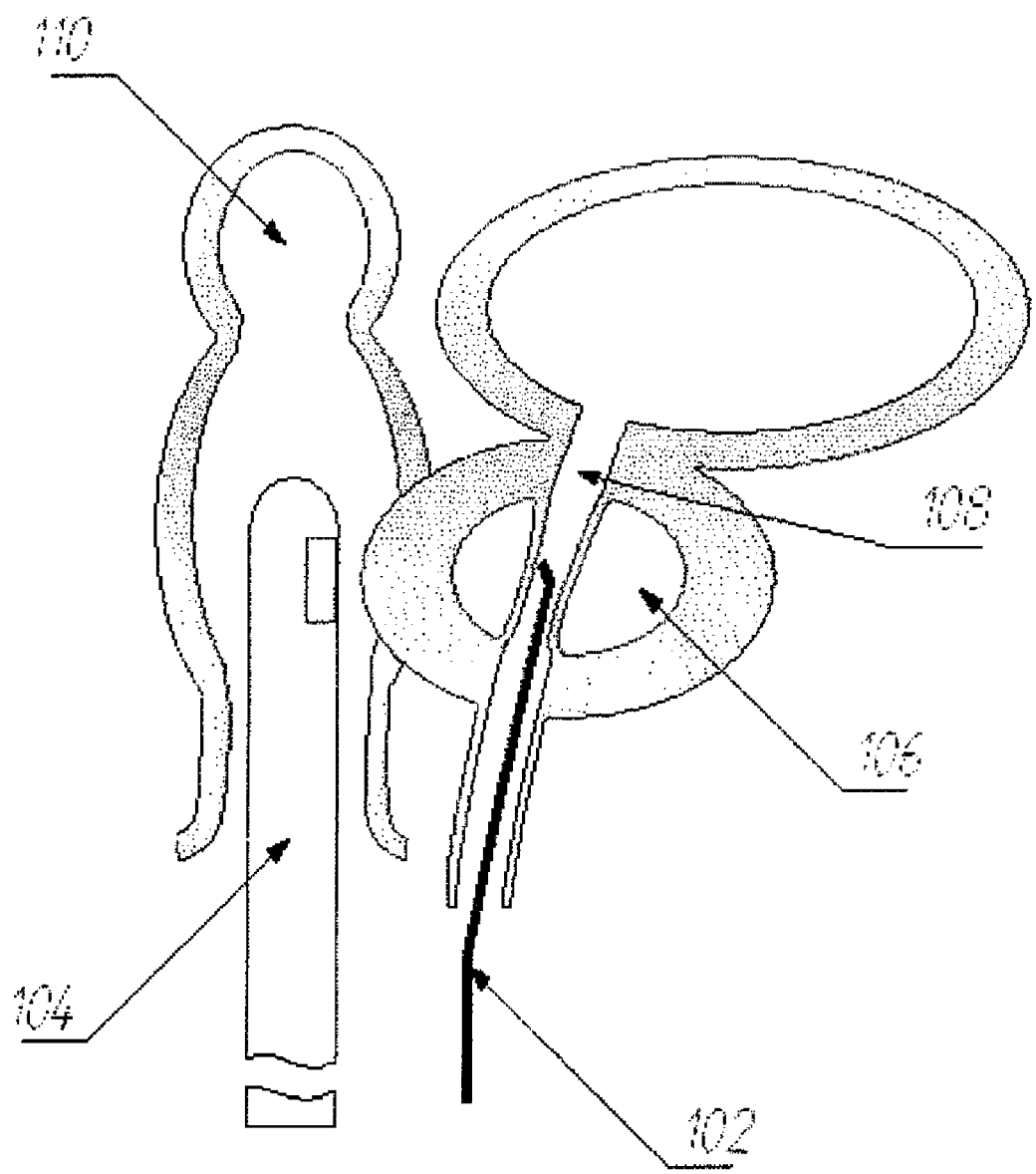
FIG. 1 shows a preferred embodiment of the present invention in which twister fiber is inserted transurethrally and treatment progress is assessed by a rectal ultrasound probe.

In a preferred embodiment for BPH procedures, depicted in FIG. 1, bent tip fiber with a fused cap 102, i.e. twister fiber, is used to convey laser radiation, and ultrasound image guidance is obtained by means of rectal probe 104 placed in the rectum 110. In order to treat hyperplasic prostate 106, twister fiber 102 is directly inserted into urethra 108, without using a cystoscope. However, if convenient, a cystoscope may be inserted along with the optical fiber. Twister fibers emit light in some preferred directions. Thus, carbonization occurs on its surface, most likely in some preferred areas. Since twister fiber is operated in contact-mode, carbonized areas at surface create hot spots that can further aid to remove tissue. As a consequence, improved and enhanced treatment of diverse pathologies can be performed, making it possible to efficiently and easily reach and treat specific tissues.

Figure 2:
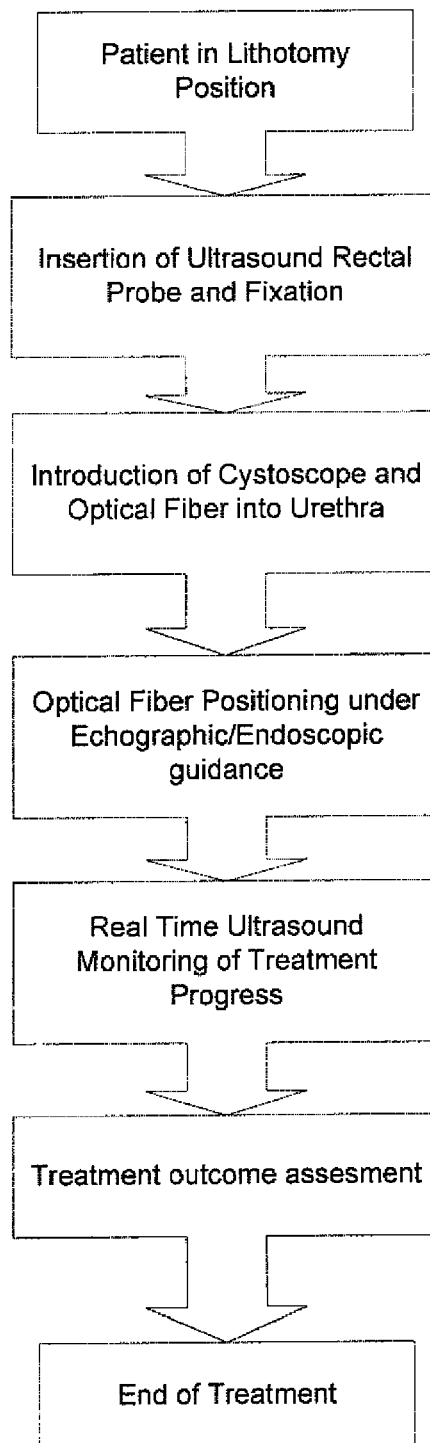
FIG. 2 depicts the main steps of a procedure according to a preferred embodiment of the present invention.

FIG. 2 shows another preferred embodiment of the present invention, sequentially describing main steps of a preferred method. Method described consists in placing an ultrasound rectal probe and fixing it by some mechanical means, with patient in lithotomy position. Then, a twister fiber is directly inserted into the urethra. Alternatively, a cystoscope with endoscopic camera and a twister fiber may be inserted into urethra. Initial positioning of laser probe may be done under endoscopic (if present) and/or ultrasound control. Laser treatment begins by operating the twister fiber probe in contact-mode. Treatment progress is monitored in real-time by the ultrasound device. In addition to BPH treatment, other applications might be the removal of tumorous (hyperplasic) tissue or other unwanted tissue in the body. To perform treatments according to the present invention, laser sources of various wavelengths can be used, but also higher power LED devices or very bright light sources.

Present invention can also be applied to other treatment techniques for treating undesired tissue. In another preferred embodiment, photodynamic therapy is used for this purpose. First, a local or systemic photosensitizer is injected into the patient, under ultrasound guidance. After a specific time interval during which photosensitizer is accumulated in the zone to be treated, a radiation of a specific wavelength is applied in order to trigger a predefined chemical reaction given by photosensitizer. This reaction will tend to eliminate undesired tissue while preserving normal tissue. Radiation can be applied interstitially, endoluminally or from the outside under ultrasound and imaging guidance, in order to precisely apply energy to target tissue. Real time treatment progress as well as damage extension can be assessed using the system disclosed.

In another preferred embodiment of the present invention, previous to carrying out radiation treatment, target tissue area (tissue to be eliminated) or volume is delimited by tracing a treatment zone in the ultrasound device and this image is stored. After delimitation, radiation is applied to the treatment zone under echographic control. As a consequence of the increase in echogenicity with temperature increase, tissue temperature can be estimated by a system that automatically and continuously compares the reference image obtained before the treatment with an image obtained during treatment. By means of this system, an audible alarm sounds when tissue outside treatment zone is beyond a certain preselected temperature value (for example, tissue coagulation temperature). In addition, alarm is triggered when elongated member's tip is near treatment zone boundary, in order to warn the physician when to stop. As another preferred embodiment, tissue delimitation is carried out on a nerve sensitive basis. In other words, after detecting nerve position, treatment zone is restricted by means of previously described techniques, in order to preserve nerves. This method has the advantage of diminishing patient pain and discomfort during and after treatment. In still another preferred embodiment, a real-time image prediction and assistance for different treatments is disclosed. The system consists in taking an image of the zone to be treated, determining the different kinds of tissues that are present in the sample and then automatically suggesting an appropriate radiation pattern, according to different criteria (physician's experience, mathematical models, etc). Imaging technology may include but is not limited to echographic, Positron Emission Tomography (PET), or Computed Tomography (CT). For noninvasive, high resolution tissue structures, optical coherence tomography may also be used. As a consequence, treatment outcome can be estimated and shown by means of simulation and prediction based on the technique to be performed. This way, physician is able to determine the optimum quantity of tissue to be extracted and visualize different estimated results. In addition, if necessary, physician can modify parameters suggested by the system, and system will re-calculate estimated results according to these changes.

It is important to mention that this image assistance system works on a real-time basis, in order to speed up the procedure and make it safer.

Despite previous system description using a twister fiber, treatment procedure disclosed can be carried out by means of different optical fiber configurations, for example, bare fibers, side fibers, etc. and utilizing different wavelengths, for instance, 810 nm, 940 nm, 980 nm, 1320 nm, 1500 nm, 1940 nm, etc. In a preferred embodiment, wavelengths of 980 nm, 1470 nm or both in an appropriate combination can be used, with power levels of 200 W or even more. For example, better and more efficient results have been obtained using a twister fiber set, having an off-axis distal end, with a 980 nm laser source in comparison to side fiber. In another example, use of a twister fiber with a laser source combining 1470 and 980 nm wavelengths results in a powerful, safe and easy BPH procedure. In both cases, due to improved efficiency, lower power levels were sufficient to obtain desired results, thus diminishing risk of damage to healthy tissue, and increasing fiber durability.

In other preferred embodiments, the present invention can combine the described treatment with a variety of local energy emitting sources, including thermal or radio frequency sources distributed at the distal end of an appropriate probe.

Having described preferred embodiments of the invention with reference to the accompanying drawings, it is to be understood that the invention is not limited to the precise embodiments, and that various changes and modifications may be effected therein by skilled in the art without departing from the scope or spirit of the invention as defined in the appended claims.

What is claimed is:

1. A method for treating and/or resecting tissue under image guidance comprising:
    inserting an imaging device selected from the group consisting of an Ultrasound device, a Positron Emission Tomography (PET) device, a Computed Tomography (CT) device and an Optical Coherence Tomography (OCT) device in an anal canal of a patient and mechanically fixing a position of the imaging device in the anal canal;
    a twister fiber, the twister fiber comprising, a bent tip fiber with a fused cap integrally placed at a distal end and a rotatable connector at the proximal side, into a urethral canal of the patient while monitoring the position of the twister fiber with the imaging device;
    delimiting a treatment zone of tissue to be treated based on an image taken by the imaging device and stored as a reference image; and
    performing a radiation treatment by delivering radiation to the tissue in the treatment zone via the twister fiber in the urethral canal while monitoring the progress of the radiation treatment with the imaging device by comparing the reference image with an image obtained during treatment.

2. The method according to claim 1, wherein said twister fiber is inserted into the urethral canal directly without an endoscope/cystoscope.

3. The method according to claim 1, wherein the twister fiber is connected to a light source selected from the group consisting of lasers, diode lasers, high power LEDs and bright lamps.

4. The method according to claim 3, wherein the light source is bright lamps and photosensitizers are applied to the tissue in said treatment zone prior to performing radiation treatment.

5. The method according to claim 1, wherein the radiation treatment comprises removal of tumorous or hyperplasic tissue or other selected tissue.

6. The method according to claim 1, wherein the radiation treatment comprises vaporization of prostatic tissue.

7. The method according to claim 1, wherein the radiation treatment comprises excavation of a prostate lobe.

8. The method of claim 1, further comprising estimating a tissue temperature by comparing the stored reference image and the image taken by the imaging device during the progress of the radiation treatment.

9. The method of claim 8, further comprising generating an audible alarm when the tissue temperature outside the treatment zone is greater than or equal to a predetermined temperature.

10. The method of claim 1, wherein delimiting the treatment zone comprises detecting a nerve position proximate the treatment zone based on nerve sensitivity, and restricting the treatment zone to preserve nerves.

11. A method for removing hyperplasic prostate tissue comprising:
    introducing an ultrasound probe for image guidance into an anal canal of a patient;
    introducing a resecting/denaturing optical fiber through a urethral canal of the patient and controlling the position of the resecting/denaturing optical fiber by using the ultrasound probe for image guidance, the resecting/denaturing optical fiber being configured to deliver light energy and wherein the resecting/denaturing optical fiber is a twister fiber, the twister fiber comprising, a bent tip fiber with a fused cap integrally placed at a distal end and a rotatable connector at the proximal side;
    determining a target tissue area of the hyperplasic prostate tissue to be removed based on an image taken through the ultrasound probe and stored as a reference image; and resecting/denaturing said hyperplasic prostate tissue by using the resecting/denaturing optical fiber in the urethral canal to deliver light energy to the target tissue area of the hyperplasic prostate tissue while monitoring the resecting/denaturing of said hyperplasic prostate tissue by using the ultrasound probe in the anal canal for image guidance by comparing the reference image with an image obtained during treatment.

12. The method according to claim 11, wherein the optical fiber is selected from the group consisting of twister fiber, bare fiber and side fiber.

13. The method according to claim 11, wherein the resecting/denaturing optical fiber is configured to deliver light energy from a light source selected from the group consisting of lasers, diode lasers, high power LEDs and bright lamps.

14. The method according to claim 13, wherein the light source is bright lamps and photosensitizers are applied to the hyperplasic prostate tissue prior to delivery of light energy.

15. The method of claim 11, further comprising estimating a tissue temperature by comparing the reference image and the image obtained through the ultrasound probe while monitoring the resecting/denaturing of said hyperplasic prostate tissue.

16. A system for removing unwanted tissue comprising:
an imaging device selected from the group consisting of an Ultrasound device, a Positron Emission Tomography (PET) device, a Computed Tomography (CT) device and an Optical Coherence Tomography (OCT) device configured to be inserted into an anal canal of a patient; and
a twister fiber, the twister fiber comprising, a bent tip fiber with a fused cap integrally placed at a distal end and a rotatable connector at the proximal side, configured to be inserted into a urethral canal of the patient and deliver light energy, the twister fiber comprising a bent fiber tip with a fused cap;
wherein the imaging device is configured to delimit a treatment zone of tissue to be removed based on an image taken through the imaging device and stored as a reference image; and
wherein the imaging device automatically provides an audible alarm if tissue outside the delimited treatment zone is beyond a preselected temperature value.

17. The system according to claim 16, wherein the system does not include an endoscope/cystoscope for inserting said twister fiber into the urethral canal.

18. The system according to claim 16, wherein said twister fiber employs a light source selected from the group consisting of lasers, diode lasers, high power LEDs, bright lamps.

* * * * *